United States Patent [19]

Anderson

[11] 3,987,183

[45] Oct. 19, 1976

[54] POLYCYCLIC IMIDAZOLES

[75] Inventor: Paul S. Anderson, Lansdale, Pa.

[73] Assignee: Merck & Co., Inc., Rahway, N.J.

[22] Filed: July 7, 1975

[21] Appl. No.: 593,411

[52] U.S. Cl.............................. 424/273; 260/309
[51] Int. Cl.$^2$..................................... C07D 235/02
[58] Field of Search..................... 260/309; 424/273

[56] References Cited

UNITED STATES PATENTS 3,624,101  11/1971  Sulkowski et al............... 260/309.6
3,814,707  6/1974   Möller et al..................... 260/309.6

OTHER PUBLICATIONS

Chemical Abstracts Subject Index E–O for vols. 11–20, p. 4443, (1917–1926).
Chemical Abstracts Subject Index Copper–I for vols. 31–40, p. 6580, (1937–1946).
Chemical Abstracts Subject Index H–MH for vols. 51–55, p. 60505, (1957–1961), (Sixth Collective Index).
Chemical Abstracts Subject Index Hy–Lit for vols. 56–65, p. 11,663s, (1962–1966), (Seventh Collective Index).
Chemical Abstracts Subject Index, Indene–Livei for vols. 66–75, p. 15770S, (1967–1971), (Eighth Collective Index).
Chemical Abstracts Chemical Substance Index (E–O), vol. 77, p. 1991CS (July–Dec. 1972).
Chemical Abstracts Chemical Substance Index (E–N), vol. 78, p. 2079CS (Jan.–June 1973).
Chemical Abstracts Chemical Substance Index (A–I), vol. 79, p. 1861CS (July–Dec. 1973).
Chemical Abstracts Chemical Substance Index (E–O), vol. 80, pp. 1977CS, 1982CS, (Jan.–June 1974).

*Primary Examiner*—Natalie Trousof
*Attorney, Agent, or Firm*—Harry E. Westlake, Jr.; James A. Arno; William H. Nicholson

[57] ABSTRACT

Disclosed are certain polycyclic imidazoles which are effective in inhibiting indoleamine-N-methyl transferase and thus useful in the treatment of mental aberrations, such as schizophrenia. Also disclosed are processes for the preparation of such imidazoles; pharmaceutical compositions comprising such compounds; and methods of treatment comprising administering such compounds and compositions.

4 Claims, No Drawings

POLYCYCLIC IMIDAZOLES

BACKGROUND OF THE INVENTION

This invention relates to certain polycyclimidazoles which by virtue of their ability to inhibit indoleamine-N-methyl transferase are useful in the treatment of certain mental aberrations in man, such as schizophrenia. This invention also relates to processes for the preparation of such polycyclicimidazoles; to pharmaceutical compositions comprising such polycyclicimidazoles; and to methods of treatment comprising administering such compounds and compositions when indicated for the treatment of mental aberrations such as schizophrenia. The polycyclicimidazoles of the present invention may be depicted by the following generic structures:

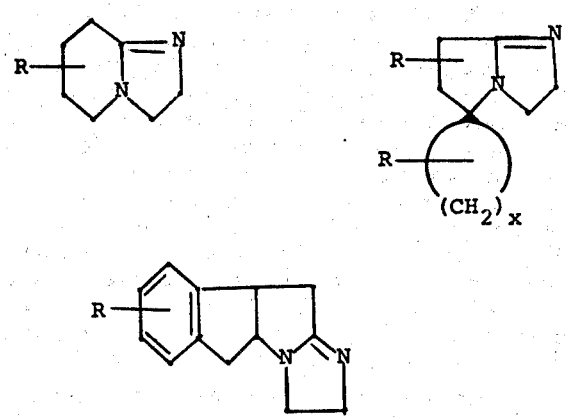

and bond isomers thereof wherein
X is an integer selected from 3, 4, or 5; and
R is selected from the group consisting of hydrogen, halogen such as chloro, lower alkyl, and loweralkoxycarbonyl.

N,N-dimethylindoleamines are generally psychotomimetic agents and some of these (e.g., dimethylserotonin and dimethyltryptamine) are reported to be product in excessive amounts by individuals with certain mental aberrations, most commonly classified as schizophrenic. Indoleamino-N-methyl transferase catalyzes the methylation steps in the biosynthesis of these compounds. Accordingly, inhibitors of this enzyme are of therapeutic value in management of the body chemistry of patients having mental aberrations such as schizophrenia and thus are useful in alleviating some of the symptoms of the disease. Thus it is an object of the present invention to provide the above-described polycyclicimidazoles and their pharmaceutically acceptable N-acid addition salts; to provide processes for the preparation of such compounds; pharmaceutical compositions comprising such compounds; and to provide methods of treatment comprising administering such compounds and compositions, when indicated for the treatment/management of mental aberrations such as schizophrenia.

DETAILED DESCRIPTION OF THE INVENTION

The preferred polycyclicimidazoles of the present invention are structurally depicted below:

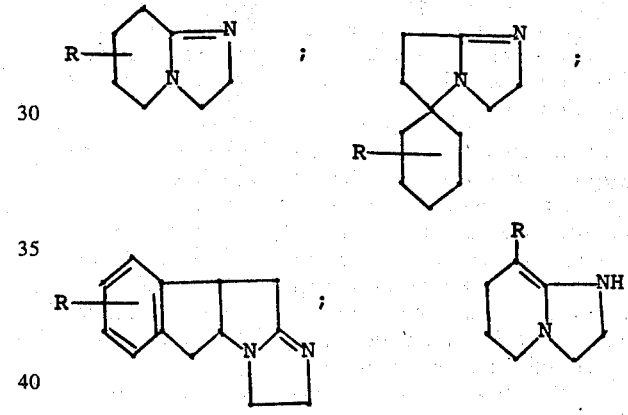

wherein R is selected from the group consisting of hydrogen, chloro, lower alkyl having from 1 to about 6 carbon atoms, and lower alkoxycarbonyl having from 2 to about 7 carbon atoms.

In general the compounds of the present invention are prepared according to the following scheme:

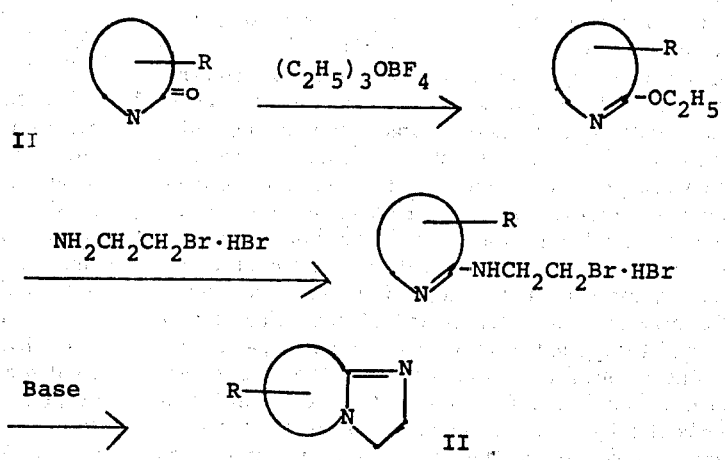

wherein R has previously been defined and wherein the cyclic lactam starting material (I) is represented by a generic symbol.

In words, relative to the above diagram, an appropriately substituted lactam (I) is treated with an alkylating agent such as trialkyloxonium fluoroborate (e.g., trimethyl-, triethyl- or the like) in a solvent such as methylenechloride, chloroform and the like at 0° to about 25° C. for from 1 to about 6 hours. The resulting lactam ether is then reacted with a 2-haloethylamine hydrohalide such as 2-bromo-ethylamine hydrobromide in a solvent such as methanol, ethanol, DMF or the like at 25° to 75° C. for from 1 to 5 hours. The resulting amidine is then cyclized to the final product II by treatment with a strong base such as an alkali metal alkoxide, for example: sodium methoxide, sodium ethoxide, or hydrous oxide such as sodium hydroxide or the like in a solvent such as methanol, ethanol, DMF or the like.

Also contemplated within the scope of the present invention are pharmaceutically acceptable N-acid addition salts of the polycyclicimidazoles of the present invention represented by structural formula II. Such pharmaceutically acceptable forms, prepared by conventional means, include: the hydrochloride, hydrobromide, sulfate, phosphate, citrate, tartrate, succinate and the like. These pharmaceutically acceptable salts of II are generally equivalent in potency to the free base form of II taking into consideration the stoichiometric quantities employed.

In the method of treatment and pharmaceutical composition aspects of the present invention, the daily dose can be from about 0.005 mg./g. to about 300 mg./kg. per day and preferably from 0.05 mg./kg. to 100 mg./kg. per day, bearing in mind, of course, that in selecting the appropriate dosage in any specific case, consideration must be given to the individual's weight, general health, metabolism, age and other factors which influence response to the drug.

Another embodiment of this invention is the provision of pharmaceutical compositions in dosage unit form which comprise from about 1 mg. to 500 mg. of a compound of the above formula.

The pharmaceutical compositions may be in a form suitable for oral use, for example, as tablets, solutions, aqueous or oily suspension, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving gents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch and alginic acid; binding agents, for example starch, gelatin or acacia, and lubricating agents, for example magnesium stearate, stearic acid or talc. The tablets may be uncoated or they may be coated by known techniques to delay disintegration and adsorption in the gastro-intestinal tract and thereby provide a sustained action over a longer period.

Formulations for oral use may also be presented as hard gelatin capsules wherein the active ingredient is mixed with an inert solid diluent, for example calcium carbonate, calcium phosphate or dalin, or as soft gelatin capsules wherein the active ingredient is dissolved or mixed with an oil or aqueous medium, for example arachis oil, liquid paraffin, olive oil or water by itself.

Aqueous suspensions or solutions containing the active compound in admixture with excipients are suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxy-cetanol, or condensation products of ethylene oxide with partial esters derived from fatty acids and a hexitol, for example polyoxyethylene sorbitol mon-oleate, or condensation products of ethylene oxide with partial esters derived from fatty acids and hexitol anhydrides, for example ployoxyethylene sorbitan mono-oleate. The aqueous suspensions may also contain one or more preservatives, for example ethyl or n-propyl, p-hydroxy benzoate, one or more coloring agents, one or more flavoring agents and one or more sweetening agents, such as sucrose, saccharin, or sodium or calcium cyclamate.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid parafin or mixtures of these. Suitable emulsifying agents may be naturally-occurring gums, for example gum acacia or gum tragacanth, naturally-occurring phosphatides, for example soya bean lecithin, and esters of partial esters derived from fatty acids and hexitol anhydrides, for example sorbitan mon-oleate, and condensation products of the said partial esters with ethylene oxide, for example polyoxyethylene sorbitan mon-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous solution or suspension. This aqueous medium may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1:3-butane oil.

The pharmaceutical compositions may be tableted or otherwise formulated so that for every 100 parts by weight of the composition there are present between 5 and 95 parts by weight of the active ingredient. The dosage unit form will generally contain between about 0.05 mg. and about 500 mg. of the active ingredient of the formulae stated above.

From the foregoing formulation discussed it is apparent that the compositions of this invention can be administered orally or parenterally. The term parenteral as used herein includes subcutaneous injection, intravenous, intramuscular, or intrasternal injection or infusion techniques. In addition, the compounds can be given rectally as suppositories or topically with penetrants.

The following examples further illustrate but do not limit the product, process, compositional or method of treatment aspects of the present invention.

EXAMPLE 1

Preparation of ethyl 1,2,3,5,6,7-hexahydroimidazo[1,2-a]-pyridine-8-carboxylate

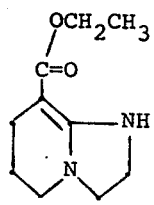

A solution of 3-carboethoxy-2-piperidone (25 g., 0.15 mole) in methylenechloride (150 ml.) is added dropwise with stirring at 0° C. to a solution of triethyloxonium fluoroborate (29 g.) in methylenechloride (150 ml.). After stirring for six hours, 33 g. of a 50% aqueous potassium carbonate solution is added and the organic layer is separated, dried over anhydrous $K_2CO_3$, filtered and concentrated under reduced pressure. Distillation of the concentrate gives 7.1 g. of the lactam ether, b.p. 90°/5 mm. which is dissolved in 100 ml. of ethanol containing 2-bromoethylamine hydrobromide (7.1 g., 0.035 mole). The solution is stirred for two days at room temperature. To this solution is added 2.1 g. of sodium methoxide. The solution is heated under reflux for one hour and then evaporated. The residue is treated with aqueous sodium hydroxide and extracted with chloroform. The chloroform solution is dried over $Na_2SO_4$, filtered and the filtrate evaporated. Distillation of the residue gives 3.5 g. of product b.p. 14°–5°/0.2 mm. which crystallizes on standing, m.p. 89°–02° C.

Analysis Calc. for: $C_{10}H_{16}N_2O_2$: Calc.: C, 61.20; H, 8.22; N, 14.28. Found: C, 61.29; H, 8.16; N, 14.21.

EXAMPLE 2

Preparation of spiro[2,3,6,7-tetrahydropyrrolo[1,2-a]-imidazole-5(5H)-1'-cyclohexane]

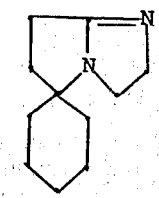

A solution of 5,5-pentamethylenepyrrolidinone (15.3 g., 0.1 mole) in methylenechloride (100 ml.) is added dropwise with stirring at 0° C. to a solution of triethyloxonium fluoroborate (24 g.) in 100 ml. of methylenechloride. Stirring is continued for 6 hours. A 50% aqueous solution of potassium carbonate (30 g.) is added with stirring. The methylene chloride solution is separated, dried over $K_2CO_3$, filtered and the filtrate evaporated. Distillation of the concentrate given 11.4 g. of the lactam ether, b.p. 95°–98°/11 mm. To the lactam ether in ethanol (150 ml.) is added 2.7 g. (.06 mole) of 2-bromoethylamine hydrobromide. The solution is heated under reflux for 2 hours and then 4.6 g. of sodium methoxide is added and heating is continued for two hours. The solvent is evaporated. The residue is treated with aqueous sodium hydroxide solution and extracted with chloroform. The chloroform extract is dried over $K_2CO_3$, filtered and the filtrate evaporated. Distillation of the concentrate gives 5.7 g. of the product b.p. 120°–125° C. /4 mm. This material is added to fumaric acid in hot isopropanol to yield on cooling the hydrogen fumarate salt m.p. 124°–125° C.

Analysis Calc. for: $C_{15}H_{22}N_2O_4$: Calc.: C, 61.20; H, 7.53; N, 9.52. Found: C, 61.09; H, 7.71; N, 9.22.

EXAMPLE 3

Preparation of 5,5a,7,8,10,10a-hexahydroindeno[1',2',4,5]-pyrrolo[1,2-a]imidazole

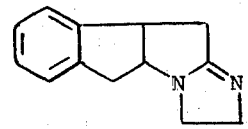

A solution of 10 g. (.06 mole) of indano[2,1-*b*]-pyrrolidin-2-one in $CH_2Cl_2$ (350 ml.) is added dropwise to a stirred solution of $(C_2H_5)_3OBF_4$ (triethyl oxonium fluoroborate), 14 g. in 50 ml. of $CH_2Cl_2$ at 0° C. and stirring is continued for 6 hours. To this solution is added 50% aqueous potassium carbonate solution (14 g.). The $CH_2Cl_2$ is decanted, dried over anhydrous $K_2CO_3$, filtered and the filtrate evaporated. The residue is recrystallized from hot hexane to yield the lactam ether (9.6 g.) which is dissolved in ethanol (150 ml.) and treated with 2-bromoethylamine hydrobromide (10 g.). The solution is heated under reflux for 2 hours and then treated with sodium methoxide (2.7 g.). After heating under reflux for 1 hour, the solvent is evaporated, the residue treated with aqueous sodium hydroxide and extracted with chloroform. The chloroform extract is dried over $Na_2SO_4$, filtered and evaporated. Distillation of the concentrate gives the product, b.p. 150°–5°/0.15 mm. which crystallized on cooling, m.p. 101°–3° C.

Analysis calc. for: $C_{13}H_{14}N_2$: Calc.: C, 78.75; H, 7.12; N, 14.13. Found: C, 78.53; H, 7.17; N, 14.03.

EXAMPLE 4

Following the procedure of Example 1, the following compounds of the present invention are prepared when the appropriate substitution (in equivalent amount) for the starting lactam of Example 1 is made:

EXAMPLE 5

Pharmaceutical compositions

A typical tablet containing 5 mg. ethyl 1,2,3,5,-6,7-hexahydroimidazo[1,2-a]pyridine-8-carboxylate per tablet is prepared by mixing together with the active ingredient calcium phosphate, lactose and starch in the amounts shown in the tables below. After these ingredients are thoroughly mixed, the dry mixture blended for an additional three minutes. This mixture is then compressed into tablets weighing approximately 129 mg. each. Similarly prepared are tablets containing spiro[2,3,6,7-tetrahydropyrrolo[1,2-a]-imidazole-5(5H)-1′-cyclohexane] and 5,5a,7,8,10,10a-hexahydroindeno[1′,2′,4,5]pyrrolo[1,2-a]-imidazole.

TABLET FORMULA

| INGREDIENT | MG. PER TABLET |
| --- | --- |
| Ethyl 1,2,3,5,6,7-hexahydroimidazo-[1,2-a]pyridine-8-carboxylate | 5 mg. |
| Calcium phosphate | 52 mg. |

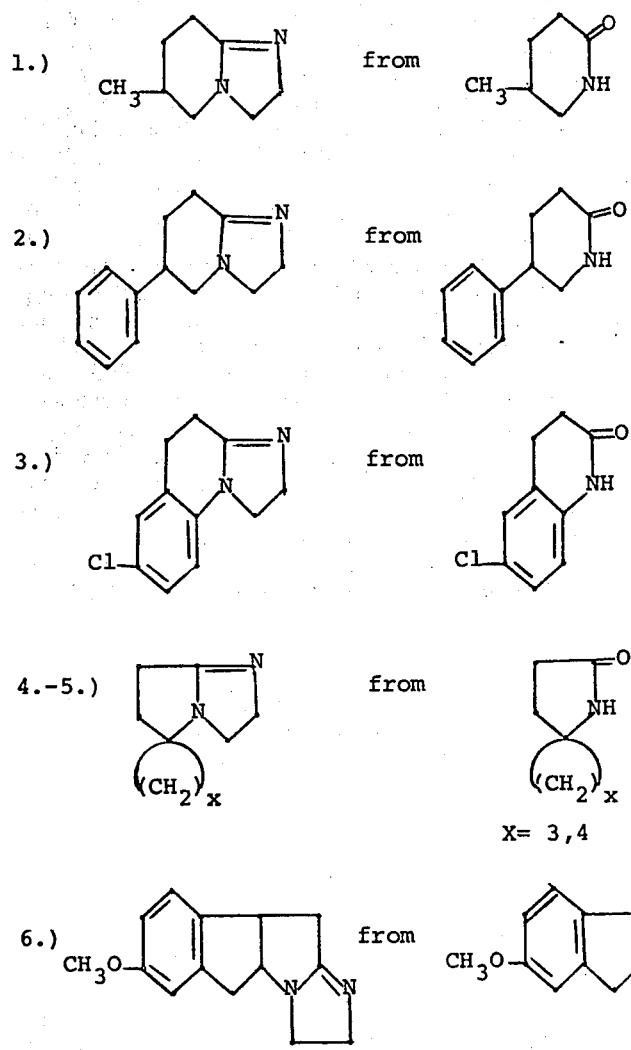

TABLET FORMULA-continued

| INGREDIENT | MG. PER TABLET |
| --- | --- |
| Lactose | 60 mg. |
| Starch | 10 mg. |
| Magnesium stearate | 1 mg. |

TABLET FORMULA

| INGREDIENT | MG. PER TABLET |
| --- | --- |
| Spiro[2,3,6,7-tetrahydropyrrolo-[1,2-a]-imidazole-5(5H)-1'-cyclohexane] | 5 mg. |
| Calcium phosphate | 52 mg. |
| Lactose | 60 mg. |
| Starch | 10 mg. |
| Magnesium stearate | 1 mg. |

TABLET FORMULA

| INGREDIENT | MG. PER TABLET |
| --- | --- |
| 5,5a,7,8,10,10a-Hexahydroindeno-[1', 2',4,5]pyrrolo[1,2-a]imidazole | 5 mg. |
| Calcium phosphate | 52 mg. |
| Lactose | 60 mg. |
| Starch | 10 mg. |
| Magnesium stearate | 1 mg. |

I claim:
1. A compound having the structure:

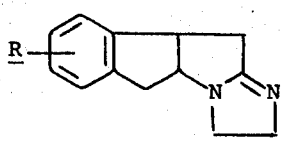

wherein
R is selected from the group consisting of hydrogen, chloro, lower alkyl,, and lower alkoxycarbonyl; and the pharmaceutically acceptable acid addition salts thereof.

2. A compound according to claim 1 which is 5,5a,7,8,10,10a-hexahydroindeno[1',2',4,5]pyrrolo[1,2-a]-imidazole.

3. A pharmaceutical composition for the treatment of schizophrenia comprising a therapeutically effective amount in unitary dosage form of a compound having the structure:

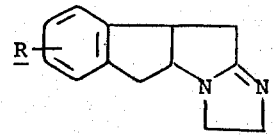

wherein
R is selected from the group consisting of hydrogen, chloro, lower alkyl, and lower alkoxycarbonyl; and the pharmaceutically acceptable acid addition salts thereof; and a pharmaceutical carrier therefor.

4. A method of treatment of schizophrenia comprising administering a therapeutically effective amount in unitary dosage form of a compound having the structure:

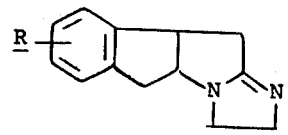

wherein
R is selected from the group consisting of hydrogen, chloro, lower alkyl, and lower alkoxycarbonyl; and the pharmaceutically acceptable N-acid addition salts thereof.

* * * * *